US00PP12237P2

(12) United States Plant Patent
Utecht

(10) Patent No.: US PP12,237 P2
(45) Date of Patent: Nov. 27, 2001

(54) GERANIUM PLANT NAMED 'FISROCKY DARK RED'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,104

(22) Filed: Jun. 1, 1999

(51) Int. Cl.[7] ..... A01H 5/00
(52) U.S. Cl. ..... Plt./330
(58) Field of Search ..... Plt./330, 325

(56) References Cited

FOREIGN PATENT DOCUMENTS

| | | |
|---|---|---|
| 98-1364 | 4/1998 | (CA) . |
| 98-26-1430 | 4/1998 | (CH) . |
| PEL 1364 | 9/1996 | (DE) . |
| 97/0962 | 9/1997 | (EP) . |
| 471 | 12/1998 | (PL) . |

OTHER PUBLICATIONS

Licensing agreement, http://www.sicasov.com/baremes/f–fl9899.htm, 1998/1999.*

UPOV–ROM GTIM Computer Database 1999/02, GTI Jouve Retrieval Software, citation for 'Fisrocky Dark Red', 1996–1998.*

Pelargonium 1998, Pelfi Fischer, Hillscheid Germany, p. 8 (1998/1999).

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of geranium plant named 'Fisrocky Dark Red', as described and illustrated, and particularly characterized by the combined features of bright red semi-double flowers; large inflorescence; dark green, slightly zoned foliage; moderately vigorous growth; and medium-early flowering response.

1 Drawing Sheet

BACKGROUND OF THE INVENTION

The present invention comprises a new and distinct cultivar of geranium plant, botanically known as *Pelargonium zonale*, and hereinafter referred to by the cultivar name 'Fisrocky Dark Red'.

'Fisrocky Dark Red' is a product of a planned breeding program which had the objective of creating new geranium varieties having dark-green foliage in combination with red flower color.

'Fisrocky Dark Red' was originated from a hybridization made by the inventor, Angelika Utecht, in a controlled breeding program in Galdar, Gran Canaria, Spain, in 1993. The female parent was a hybrid seedling, designated no. 1477/2, having bright red, single flowers, dark-green foliage, and weak growth. The female parent was originally derived from crosses between older commercial varieties, 'Osna' with 'Yours Truly', and 'Gartendirektor Ries' with 'Bolero' (U.S. Plant Pat. No. 5,939). The male parent of 'Fisrocky Dark Red' was the variety 'Fissamba' (U.S. Plant Pat. No. 10,364), which was characterized by bright-red, compact, round inflorescence, medium-green foliage with distinct zonation and relatively compact plant habit.

'Fisrocky Dark Red' was selected as one flowering plant within the progeny of the stated cross by the inventor, Angelika Utecht, in 1994 in a controlled environment in Galder, Gran Canaria, Spain.

The first act of asexual reproduction of 'Fisrocky Dark Red' was accomplished when vegetative cuttings were taken from the initial selection in autumn 1994 in a controlled environment in Galdar, Gran Canaria, Spain by Angelika Utecht. Horticultural examination of plants grown from these cuttings, initiated in May 1995 in Hillscheid, Federal Republic of Germany, and continuing thereafter, has demonstrated that the combination of characteristics as herein disclosed for 'Fisrocky Dark Red' are firmly fixed and are retained through successive generations of asexual reproduction.

BRIEF DESCRIPTION OF THE INVENTION

The following traits have been repeatedly observed and are determined to be basic characteristics of 'Fisrocky Dark Red', which in combination distinguish this geranium as a new and distinct cultivar:

1. Intense red, semi-double flowers;
2. Relatively large, semi-spherically shaped umbels and dark-red peduncles;
3. Dark-green foliage with slight zonation;
4. Vigorous growth and moderately tall plant habit; and
5. Medium flowering response.

'Fisrocky Dark Red' has not been observed under all possible environmental conditions. The phenotype of the new cultivar may vary significantly with variations in environment such as temperature, light intensity and daylength without any change in the genotype of the plant. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fisrocky Dark Red' are the paternal variety 'Fissamba' and the variety 'Tango' (U.S. Plant Pat. No. 5,933).

In comparison of 'Fissamba', 'Fisrocky Dark Red' has flowers of similar color and shape but larger inflorescence. 'Fisrocky Dark Red' has dark-red peduncles, whereas 'Fissamba' has green to light red peduncles. Furthermore, 'Fisrocky Dark Red' has dark-green foliage, larger leaves, and grows more vigorously than 'Fissamba'.

In comparison to 'Tango', 'Fisrocky Dark Red' has peduncles that are dark-red colored and 25–30% shorter than the peduncles of 'Tango', which are mainly green. The umbels of 'Tango' are borne higher above the foliage. Furthermore, foliage of 'Fisrocky Dark Red' is slightly darker-green with more distinct zonation, and flowering begins somewhat earlier than 'Tango'.

BRIEF DESCRIPTION OF THE DRAWING

The accompanying photographic drawing shows typical flower and foliage characteristics of 'Fisrocky Dark Red' with colors being as true as possible will illustrations of this type.

DETAILED BOTANICAL DESCRIPTION

The measurements were taken in Langley, British Columbia, Canada, on May 26, 1998, 10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheid, Germany.

Classification:

*Botanical.*—A hybrid of the species *Pelargonium zonale L'Hérit.*

*Commercial.*—Zonal geranium, cv. 'Fisrocky Dark Red'.

Inflorescence:

*Umbel.*—Shape: Large, flat and semi-spherical. Average diameter: 119 mm. Average depth: 65 mm. Peduncle length: 128 mm, often with a 'knot' or 'joint' near the base. Peduncle color: Light to dark-red, approximately RHS 183 A or lighter. Peduncle texture: Normally thick/strong, appears slightly rough or velvety due to the short pubescence. Pedicel length: 30 mm. Pedicel color: Light to dark-red, approximately RHS 178 A. Number of flowers per umbel: More than 30. Lastingness of the individual umbel: Large, wide and consisting of many individual flowers that open one by one so the umbel lasts longer than the average zonal variety, lasting approximately 18 days in greenhouse conditions in spring at a temperature of 18° C.

*Corolla.*—Average diameter: 46 mm. Form: Semi-double. Shape: Round, flat and cup-shaped. Number of petals: 7–9. Number of petaloids: 1–3. Color (general tonality from a distance of three meters): Intense red. Color of upper petals: RHS 43 A. Markings of upper petals: Short veins at the base; hardly visible; slightly darker-red, RHS 45 A, than the main color of the petal. Color of lower petals: RHS 46 B. Color of lower surface of petals: RHS 43 A–B. Color of sepals: Basal part is dark-red, RHS 185 A or lighter, tips are green RHS 143 A. Number of sepals: 5. Texture of sepals: Smooth at the tips with slight, very short pubescence in the middle part.

*Bud (just before petals unfold).*— Shape: Broad and elliptical. Color (sepals): Mainly green, RHS 143 B–144 A, the base is dark-red. Color (petals): Bright red, RHS 45 B. Length: Approximately 20 mm. Width: Approximately 13 mm.

*Reproductive organs.*—Androecium: 5–7 fertile anthers, white to light-pink filaments, yellow-orange pollen. Gynoecium: 5–6-lobed stigma, dark-red stigma and style, RHS 46 A. Fertility/seed set: Occasionally, few seeds are developed.

*Spring flowering response period.*—In Hillscheid, Germany, in 1998, plants had on average 0.7 flowers opened 12 weeks after planting of unrooted cuttings.

*Outdoor flower production.*—Medium.

*Blooming habit.*—Continuous flowering from about May to mid-September; after which flowering may be poor depending on general conditions and light intensity. There is no noticeable fragrance apart from the slightly aromatic scent that can be noticed when flowers are crushed.

*Lastingness of the individual bloom.*—Approximately 9 days in greenhouse conditions in spring at a temperature of 18° C.

*Durability.*—Good shatter resistance, relatively good rain resistance.

Plant:

*Foliage.*—Form: Kidney-shaped, with an open base. Margin: Bicrenated, somewhat wavy. Size of leaf: 92 mm. Texture: Slightly velvety and dull (not glossy). Color of upper surface: Dark-green, approximately RHS 137 B. Color of lower surface: RHS 137 C. Color of zonation: Brown, approximately RHS 166 A; distinctness is 3 (in the range from 1="no zonation" to 9="very strong"). Tolerance of botrytis: Average.

*General appearance and form.*—Internode length: 15 mm. Branching pattern: 5.9 naturally-occurring branches. Size of foliage: 16.1 cm high and 31.1 cm in diameter.

I claim:

1. A new and distinct cultivar of geranium plant named 'Fisrocky Dark Red', as described and illustrated.

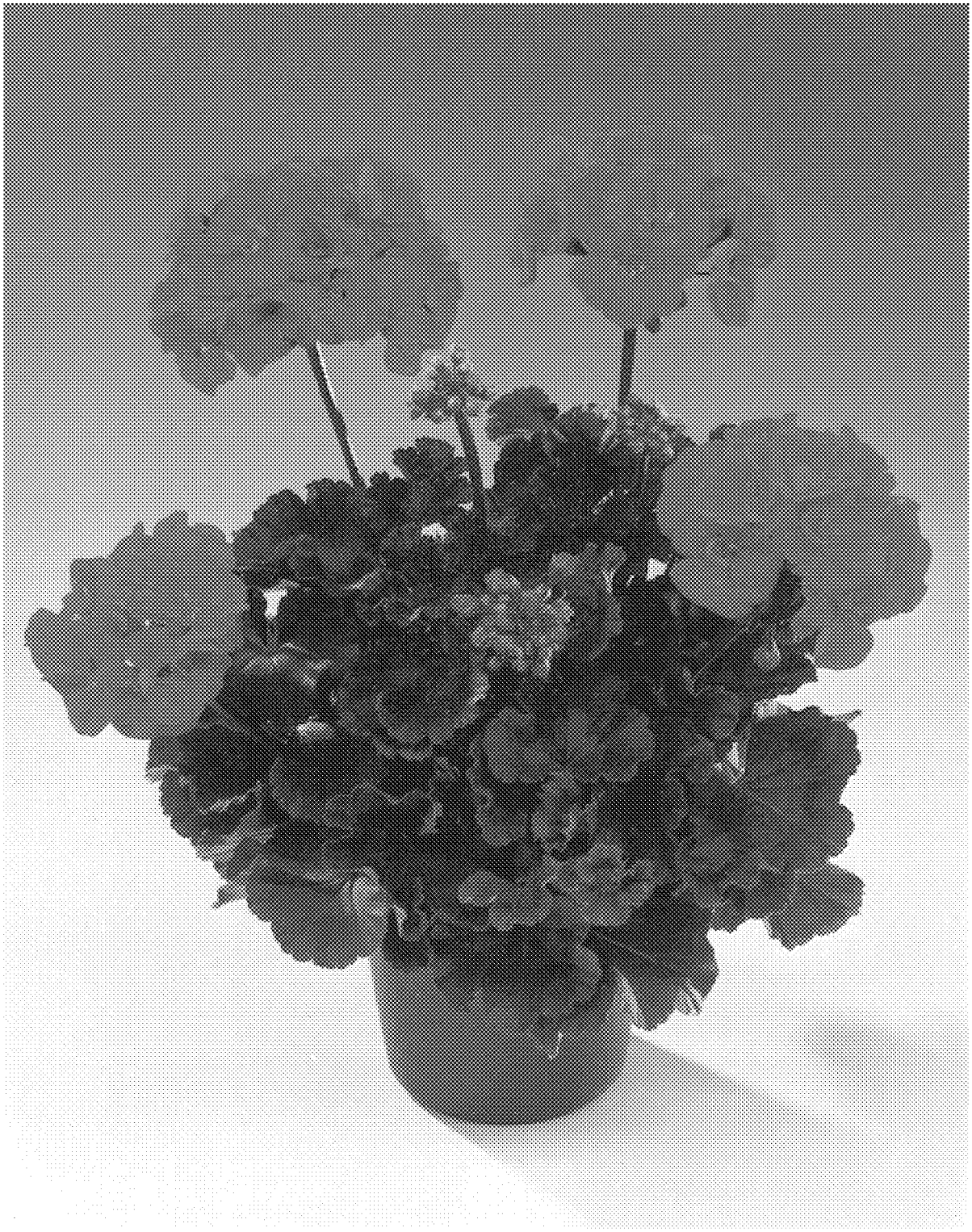

* * * * *